United States Patent [19]

Ziemecki et al.

[11] Patent Number: 6,080,884
[45] Date of Patent: Jun. 27, 2000

[54] AMINONITRILE PRODUCTION

[75] Inventors: Stanislaw Bogdan Ziemecki, Wilmington; Alex Sergey Ionkin, Newark, both of Del.

[73] Assignee: E. I. du Pont de Nemours and Company, Wilmington, Del.

[21] Appl. No.: 09/268,147

[22] Filed: Mar. 15, 1999

Related U.S. Application Data

[60] Provisional application No. 60/078,715, Mar. 20, 1998.

[51] Int. Cl.$^7$ ................................. C07C 255/02
[52] U.S. Cl. ............................................ 558/459
[58] Field of Search ............................ 558/759

[56] References Cited

U.S. PATENT DOCUMENTS

| | | | |
|---|---|---|---|
| 2,208,598 | 7/1940 | Rigby | 260/464 |
| 2,245,129 | 6/1941 | Greenewalt | 260/2 |
| 2,257,814 | 1/1941 | Rigby | 260/464 |
| 2,762,835 | 9/1956 | Swerdloff | 260/465.5 |
| 3,322,815 | 5/1967 | Feldman et al. | 260/465.5 |
| 3,591,618 | 7/1971 | Hanschke | 260/464 |
| 4,248,799 | 2/1981 | Drake | 564/491 |
| 4,389,348 | 6/1983 | Diamond et al. | 260/465.5 R |
| 4,568,736 | 2/1986 | Curatolo et al. | 528/313 |
| 4,601,859 | 7/1986 | Galle et al. | 558/459 |
| 5,151,543 | 9/1992 | Ziemecki | 558/459 |
| 5,296,628 | 3/1994 | Sanchez | 558/452 |
| 5,512,697 | 4/1996 | Schnurr et al. | 558/459 |
| 5,527,946 | 6/1996 | Flick et al. | 558/459 |

FOREIGN PATENT DOCUMENTS

| | | |
|---|---|---|
| 681932 | 11/1966 | Belgium . |
| 0 077 911 | 5/1983 | European Pat. Off. . |
| 0 161 419 | 11/1985 | European Pat. Off. . |
| 836 938 | 4/1952 | Germany . |
| 848 654 | 9/1952 | Germany . |
| 1543794 | 1/1970 | Germany . |
| 196 36 768 A1 | 3/1998 | Germany . |
| WO 92/21650 | 12/1992 | WIPO . |

OTHER PUBLICATIONS

PCT International Search Report dated Aug. 5, 1999 for PCT/US99/06044.

Mares et al., Preparation and Characterization of a Novel Catalyst for the Hydrogenation of Dinitriles to Aminonitriles, *Journal of Catalysis*, 112, 145–156, Apr. 20, 1987; revised Nov. 3, 1987.

*Primary Examiner*—Joseph McKane
*Assistant Examiner*—Joseph Murray

[57] ABSTRACT

A process for selectively hydrogenating a dinitrile to an aminonitrile is provided. The process comprises contacting a dinitrile with a hydrogen-containing fluid in the presence of a solvent and a metal catalyst in which the solvent comprises liquid ammonia, an alcohol, ammonium hydroxide, or combinations thereof and the metal catalyst comprises nickel and iron and can be supported on an inorganic support such as, for example, magnesium oxide.

17 Claims, No Drawings

AMINONITRILE PRODUCTION

This application is based on provisional application No. 60/078,715 filed Mar. 20, 1998.

FIELD OF THE INVENTION

The invention relates to a selective hydrogenation process for producing aminonitriles.

BACKGROUND OF THE INVENTION

Aminonitriles are a class of important chemicals which have a variety of industrial applications. For example, aminonitriles can be used as a monomer for producing high molecular weight polymers. Specifically, 6-aminocapronitrile can be used to produce nylon 6.

Aminonitriles can be produced by catalytic hydrogenation of dinitriles. However, the yield of and selectivity to a desired aminonitrile using processes known to one skilled in the art are generally not as high as one skilled in the art desires. Additionally, the amount of the complete hydrogenation product, diamine, is generally higher than one skilled in the art would desire.

A convenient process resulting in a high yield of aminonitriles at low levels of dinitrile starting material, fully hydrogenated products (diamines), and byproducts would be of great usefulness for commercial production of aminonitriles.

Therefore, there is an increasing need to develop a process that can selectively hydrogenate a dinitrile to aminonitrile.

SUMMARY OF THE INVENTION

It is the object of the present invention to provide a process for the preparation of aminonitriles from dinitriles. An advantage of this invention is that an aminonitrile can be produced in high yield and high selectivity to the aminonitrile. Other objects and advantages will become more apparent as the invention is more fully disclosed hereinbelow.

This invention provides a process for the selective or partial hydrogenation of a dinitrile to an aminonitrile. The process comprises contacting a dinitrile with a hydrogen-containing fluid in the presence of (a) a solvent comprising liquid ammonia, an alcohol, ammonium hydroxide, or combinations of two or more thereof and (b) a metal catalyst comprising a metal selected from the group consisting of nickel, iron, cobalt, and combinations of two or more thereof. The process can further comprise recovering the aminonitrile.

DETAILED DESCRIPTION OF THE INVENTION

According to this invention, a dinitrile having the formula of NCRCN is contacted with a hydrogen-containing fluid in the presence of a solvent and a metal catalyst in which R is a hydrocarbylene group selected from the group consisting of alkylene group, arylene group, alkenylene group, alkarylene group, aralkylene group, and combinations of two or more thereof. The presently preferred R is an alkylene group. Each hydrocarbylene group can contain 1 to about 25, preferably 1 to 15, and most preferably about 2 to about 10 carbon atoms per group. In other words, a suitable dinitrile can contain 3 to about 27, preferably 3 to about 17, and most preferably about 4 to about 12 carbon atoms per dinitrile molecule.

Examples of suitable dinitriles include, but are not limited to, adiponitrile, methylglutaronitrile, dodocamethylenedinitrile, propanedinitrile, butanedinitrile, pentanedinitrile, heptanedinitrile, nonanedinitrile, dodecanedinitrile, pentadecanedinitrile, icosanedinitrile, tetracosanedinitrile, 3-methylhexanedinitrile, 3-methylene hexanedinitrile, 2-methyl-4-methyleneoctanedinitrile, and combinations of two or more thereof The presently preferred dinitrile is adiponitrile because its selective hydrogenation product, 6-aminocapronitrile is a well-known monomer for polymerization applications.

Any hydrogen-containing fluid can be used in the invention as long as there is sufficient hydrogen in the fluid to selectively hydrogenate a dinitrile to a mononitrile. The term "fluid" refers to liquid, gas, or both. The hydrogen content in the fluid can range from 1 to 100%, preferably about 50 to about 100%, and most preferably 90 to 100% by volume. The presently preferred hydrogen-containing fluid is a pure hydrogen gas.

The molar ratio of hydrogen (in the hydrogen-containing fluid) to dinitrile is not critical as long as there is sufficient hydrogen present to produce the desired aminonitrile. Hydrogen is generally used in excess. Hydrogen pressures are generally in the range of from about 50 to about 2,000 psi (0.345 to 13.79 MPa), with about 200 to about 1,000 psi (1.42 to 6.89 MPa) preferred.

Any solvent that comprises liquid ammonia, an alcohol, or combinations thereof can be used in the invention. The concentration of liquid ammonia in the solvent can range from about 20 to about 100%, preferably about 50 to about 100%, and most preferably about 80% to about 100%. A pure liquid ammonia is presently preferred. The molar ratio of ammonia to dinitrile can generally be in the range of from about 1:1 to about 30:1, preferably about 2:1 to about 20:1.

The concentration of alcohol in the solvent can be in the range of from about 20 to about 95 and preferably about 30 to about 90 weight %, based on the weight of total solvent. The presently preferred alcohols are aliphatic alcohols containing from one to about 10, preferably 1 to about 5 carbon atoms. The alcohol can be present in the solvent in an amount that can improve the selectivity to an aminonitrile in a selective hydrogenation of dinitrile. Generally the molar ratio of alcohol to dinitrile can be in the range of from about 1:1 to about 30:1, preferably about 2:1 to about 20:1, and most preferably 3:1 to 20:1.

If ammonium hydroxide is employed as a solvent, the molar ratio of ammonia in the ammonium hydroxide to dinitrile can be the same as the molar ratio of liquid ammonia to dinitrile.

A base is generally present in an alcohol solvent to improve the selectivity to an aminonitrile in the selective hydrogenation of a dinitrile. The base is substantially soluble in the solvent or the selective hydrogenation medium and preferably has the $pK_b$ value of at most 5. The term "substantialy" means more than trivial. Suitable base can be an inorganic base, an organic base, or combinations thereof. Suitable inorganic bases can include ammonia, ammonium hydroxide, alkali metal hydroxides, alkali metal methoxides, alkali metal carbonates, alkaline earth metal hydroxides, alkaline earth metal methoxides, alkaline earth metal carbonates, or combinations of two or more thereof The presently preferred inorganic bases are ammonia, lithium hydroxide, sodium hydroxide, and potassium hydroxide. The preferred organic bases are 1,5 diazabicyclo [4.3.0] non-5-ene ("DBN") and 1,8-diazabicyclo [5.4.0] undec-7-ene ("DBU"). The most preferred base is liquid ammonia. The chosen base should be soluble in the medium for the hydrogenation reaction. It was found to be beneficial to have between 1 and 10 weight % (relative to the amount of hydrogenated dinitrile) of such base present in the reaction mixture. Increased concentration of the base accelerates the rate of dinitrile conversion and improves selectivity to the aminonitrile by limiting the amount of undesirable byproducts. In the absence of an inorganic base in the reaction mixture the hydrogenation process is slow, and increased amounts of undesired products of condensation may be formed.

The metal catalyst comprises a catalytically active metal selected from the group consisting of nickel, cobalt, iron, and combinations of two or more thereof. The metal catalyst can also be used together with one or more promoters such as, for example, chromium, molybdenum, tungsten, and combinations of two or more thereof.

The metal catalyst can also be supported on an inorganic support such as alumina, magnesium oxide, and combinations thereof. The catalyst can be supported on an inorganic support by any means known to one skilled in the art such as, for example, impregnation, coprecipitation, ion exchange, and combinations of two or more thereof. The presently preferred inorganic support is magnesium oxide for it is effective in the selective hydrogenation.

The metal catalyst, supported or unsupported, can be present in any physical shapes or forms. It can be in fluidizable forms, extrudates, tablets, spheres, or combinations of two or more thereof.

The molar ratio of the metal catalyst to dinitrile can be any ratio as long as the ratio can catalyze the selective hydrogenation of a dinitrile. The ratio generally can be in the range of from about 0.0001:1 to about 1:1, preferably about 0.001:1 to about 0.5:1. If the metal catalyst is supported on an inorganic support or is a portion of an alloy or solid solution, the metal catalyst can be present in the selective hydrogenation medium in the range of from about 0.1 to about 60, preferably about 1 to about 50, and most preferably about 2 to about 20 weight %, based on the total weight of metal catalyst and and inorganic support.

The process of the present invention can be carried out at a temperature in the range of from about 25 to 150° C., preferably 40 to 100° C., most preferably 60 to 80° C. at a total pressure from about 50 to about 2000 psi (0.345 to 13.79 MPa), preferably about 200 to about 1000 psi (1.42 to 6.89 Mpa) for about 15 minutes to about 25 hours, preferably about 0.5 to about 10 hours.

The process of the invention can be operated batch wise or continuously in an appropriate reactor or vessel known to one skilled in the art. Stirring or agitation of the reaction mixture can be accomplished in a variety of ways known to those skilled in the art. The partial hydrogenation of the starting dinitrile to the corresponding aminonitrile with high selectivity at high conversions of the dinitrile makes this process efficient and useful.

The following examples further illustrate the process of the invention and are not to be construed to unduly limit the scope of the invention.

EXAMPLES

General Procedures:

A heated autoclave (50 ml), equipped with a stirrer, was charged with dinitrile containing about 0.5 to about 2% of a N-methyl pyrrolidinone (by weight of dinitrile) as an internal standard, a catalyst, and solvent. During the run, samples were extracted using a sampling line equipped with a metal frit filter, and analyzed by GC.

Definitions:

The meaning of terms used in the Examples is defined as follows:

Yield of aminonitrile is the measured concentration of aminonitrile divided by the starting concentration of dinitrile.

Conversion of the dinitrile is the difference between the starting and the instant concentration of dinitrile, divided by the starting concentration of dinitrile.

Selectivity to aminonitrile is the measured yield of aminonitrile divided by conversion of the dinitrile at that instance.

Experiment 1

Preparation of NiFe/MgO catalysts

Distilled water (100 ml) was heated with stirring on a hot plate almost to the boiling point. The calculated amounts of nitrates of Fe(III) and Ni(II) were added together and at once. The nitrates dissolved after a few seconds of stirring. The solution was colored and had a pH of approximately 5. Magnesium oxide (Alfa Aesar, Ward Hill, Mass.) (3 g) was added slowly over several minutes to avoid boiling over of the solution. The heat was turned off, but vigorous stirring was continued for another 1–2 hours to allow for complete mixing and adsorption. The pH of the mixture at this point was about 11. After gradual cooling of the suspension, the reaction mixture was filtered and the solids were washed with distilled water. The washed solids were dried overnight in a vacuum oven (0.1 mm Hg) set at 115° C.–120° C. The dried solid was ground with a mortar and pestle and was hereinafter referred to as ground catalyst or catalyst precursor.

The ground catalyst precursor was generally activated by heating in a tube furnace, in a flow of hydrogen of approximately 40 cc/min. The temperature was slowly raised to 480° C., then kept at that level overnight (ca. 14 hours). The reduced catalyst was cooled in a flow of hydrogen, then unloaded and stored in a dry box.

Examples 1–6

Hydrogenation of Adiponitrile to Aminocapronitrile with NiFe/MgO Catalyst

Example 1

Catalyst containing 35% of nickel and 2.5% of iron by weight was prepared and activated according to the method of Experiment 1. The activated catalyst was kept in a dry box.

A portion of the activated catalyst (1.2 g) was loaded into a 50 cc autoclave, then 3.2 g of adiponitrile containing a N-methyl pyrrolidinone internal standard was added, followed by 35 mL (21 g) of liquid ammonia as solvent and hydrogen. The autoclave was operated at 70° C. and 1000 psig total (hydrogen+ammonia) pressure, with liquid samples being withdrawn for analysis via a filter. The maximum yield of the aminocapronitrile (71.3%) was reached after 1.2 hrs from the start of reaction. At that time conversion of adiponitrile was 89%. Thus, selectivity to aminocapronitrile was 79.6%. The impurities detected were: about. 60 ppm of hexamethylene imine, 0.67% of 2-cyclopentylidene imine, 0.43% of cyanovaleroamide, and ca. 0.5% bishexamethylenetriamine.

Additional five runs with catalysts shown in the table and 3.5 g of adiponitrile in each runs were similarly carried out. The results of the runs are summarized in the following below.

Example 2

Catalyst precursor containing 25% Ni and 5% Fe by weight deposited on MgO, was prepared according to the

| Example No. | Catalyst (g) | Time (minute) | Yield (%) | Selectivity (%) | ADN Conversion |
|---|---|---|---|---|---|
| 1 | 35%Ni2.5%Fe/MgO (1.2) | 72 | 71.3 | 79.6 | 89% |
| 2 | 25%Ni5%Fe/MgO (0.6) | 90 | 71 | 80 | 90 |
| 3 | 35%Ni5%Fe/MgO (0.6) | 120 | 75 | 81.5 | 92 |
| 4 | 35%Ni/MgO (0.6) | 80 | 72 | 76 | 94 |
| 5 | 15%Ni/MgO (0.6) | 240 | 75 | 80 | 93 |
| 6 | 25%Ni/MgO (0.6) | 120 | 75.4 | 82 | 92 | method of the Experiment 1. This catalyst was activated in a flow of hydrogen as described in Example 1, and was unloaded and stored in a dry box. 0.6 g of this catalyst was charged into a 50 mL autoclave, followed by 35 mL of deaerated methanol containing 10% of ADN and the internal standard. To that 0.5 g of the 50% NaOH solution was added. The autoclave was pressurized to 500 psig with hydrogen, and temperature raised to 70° C. with stirring. The maximum yield of aminocapronitrile, 71%, was reached after 1.5 hrs on stream, at ADN conversion ca. 90%. Thus the selectivity to aminocapronitrile approaches 80% at that time.

Example 3

A catalyst containing 35% Ni and 5% Fe by weight, deposited on MgO, was prepared and activated as described in Experiment 1 and Example 1 above. 0.6 g of this catalystwas added to a 50 mL autoclave, together with 35 mL of deaerated methanol containing 10% of ADN and the internal standard. To that 0.5 g of standard 50% NaOH solution was added. The autoclave was pressurized to 500 psig with hydrogen, and temperature raised to 70° C. with stirring. The full conversion of ADN was reached after ca. 3 hrs on stream. The maximum yield of aminocapronitrile was 75% at ca. 92% ADN conversion. Thus the selectivity to aminocapronitrile was 81.5% at that time.

Example 4

A catalyst containing 35% Ni by weight, and no Fe, deposited on MgO, was prepared and activated as described in Experiment 1 and Example 1 above. The autoclave was charged and operated as described in Example 3 above. The maximum yield of aminocapronitrile was 72% at ca. 94% ADN conversion. Thus the selectivity to aminocapronitrile was ca. 76% at that time.

Example 5

A catalyst containing 15% Ni by weight, and no Fe, deposited on MgO, was prepared and activated as described in Experiment 1 and Example 1 above. The autoclave was charged and operated as described in Example 3 above. The maximum yield of aminocapronitrile was 75% at ca. 93% ADN conversion. Thus the selectivity to aminocapronitrile was ca. 80% at that time. Quantitative conversion of ADN was achieved after 6 hrs on stream.

Example 6

A catalyst containing 25% Ni by weight, and no Fe, deposited on MgO, was prepared and activated as described in Experiment 1 and Example 1 above. The autoclave was charged and operated as described in Example 3 above. The maximum yield of aminocapronitrile was 75.4% at ca. 92% ADN conversion. Thus the selectivity to aminocapronitrile was ca. 82% at that time. Quantitative conversion of ADN was achieved after 2 hrs and 40 min. on stream.

Pertinent results of the above examples are summarized in the following table.

What is claimed is:

1. A process for producing an aminonitrile from a dinitrile comprising contacting a dinitrile with a hydrogen-containing fluid in the presence of a solvent and a metal catalyst wherein said solvent is selected from the group consisting of liquid ammonia, alcohol, ammonium hydroxide, and combinations of two or more thereof; said catalyst comprises a metal selected from the group consisting of nickel, cobalt, iron, and combinations of two or more thereof; and said catalyst is supported on magnesium oxide.

2. A process according to claim 1 wherein said dinitrile is an aliphatic dinitrile.

3. A process according to claim 2 wherein said dinitrile has about 4 to about 12 carbon atoms per molecule.

4. A process according to claim 1 wherein the molar ratio of said solvent to said dinitrile is in the range of from about 1:1 to about 30:1.

5. A process according to claim 1 wherein the molar ratio of said solvent to said dinitrile is in the range of from about 2:1 to about 20:1.

6. A process according to claim 3 wherein the molar ratio of said solvent to said dinitrile is in the range of from about 2:1 to about 20:1.

7. A process according to claim 1 wherein said dinitrile is selected from the group consisting of adiponitrile, ethylsuccinonitrile, methylglutaronitrile, dodecanedinitrile, and combinations of two or more thereof.

8. A process according to claim 5 wherein said dinitrile is selected from the group consisting of adiponitrile, ethylsuccinonitrile, methylglutaronitrile, dodecanedinitrile, and combinations of two or more thereof.

9. A process according to claim 8 wherein said solvent is liquid ammonia.

10. A process according to claim 1 wherein said solvent is an aliphatic alcohol comprising a base.

11. A process according to claim 10 wherein said base is selected from the group consisting of ammonia, ammonium hydroxide, alkali metal hydroxides, alkali metal methoxides, alkali metal carbonates, alkali metal carbonate, alkaline earth metal hydroxides, alkaline earth metal methoxides, alkaline earth metal carbonates, alkaline earth metal carbonate, and combinations of two or more thereof.

12. A process for producing an aminonitrile from a dinitrile comprising contacting a dinitrile with hydrogen in the presence of (1) a solvent selected from the group consisting of liquid ammonia, aliphatic alcohol, ammonium hydroxide, and combinations of two or more thereof and (2) a metal catalyst comprising nickel and iron supported on magnesium oxide, to effect the production of an aminonitrile wherein said dinitrile has about 4 to about 12 carbon atoms per molecule; and the molar ratio of said solvent to said dinitrile is in the range of from about 2:1 to about 20:1.

13. A process according to claim 12 wherein said dinitrile is selected from the group consisting of adiponitrile, ethylsuccinonitrile, methylglutaronitrile, dodecanedinitrile, and combinations of two or more thereof; and said solvent is liquid ammonia.

14. A process according to claim 12 wherein said dinitrile is selected from the group consisting of adiponitrile, ethylsuccinonitrile, methylglutaronitrile, dodecanedinitrile, and combinations of two or more thereof; and said solvent is an aliphatic alcohol which comprises a base.

15. A process for selectively hydrogenating adiponitrile to aminocaponitrile comprising contacting, at a temperature in the range of from about 60° C. to about 80° C. under a pressure in the range of from about 200 to about 1,000 pounds per square inch (1.72 to 6.89 Mpa), said adiponitrile with hydrogen in the presence of (1) a solvent which comprises either liquid ammonia or an aliphatic alcohol comprising a base and (2) a catalyst comprising iron and nickel wherein said catalyst is supported on magnesium oxide and is in the range of from about to 25 to about 35% based on the total weight of said catalyst and magnesium oxide, and the molar ratio of said solvent to said adiponitrile is in the range of from about 2:1 to about 20:1.

16. A process according to claim 15 wherein said solvent is liquid ammonia and said process further comprises recovering said aminocapronitrile.

17. A process according to claim 15 wherein said solvent is an aliphatic alcohol comprising a base and said process further comprises recovering said aminocapronitrile.

* * * * *